(12) United States Patent
Leung et al.

(10) Patent No.: US 10,369,373 B2
(45) Date of Patent: Aug. 6, 2019

(54) PORTABLE TRANSCUTANEOUS MAGNETIC STIMULATOR AND SYSTEMS AND METHODS OF USE THEREOF

(71) Applicant: The Regents of the University of California, Oakland, CA (US)

(72) Inventors: Albert Leung, La Jolla, CA (US); Shiv Shukla, La Jolla, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 235 days.

(21) Appl. No.: 14/775,490

(22) PCT Filed: Mar. 11, 2014

(86) PCT No.: PCT/US2014/023808
§ 371 (c)(1),
(2) Date: Sep. 11, 2015

(87) PCT Pub. No.: WO2014/164926
PCT Pub. Date: Oct. 9, 2014

(65) Prior Publication Data
US 2016/0015995 A1 Jan. 21, 2016

Related U.S. Application Data

(60) Provisional application No. 61/776,050, filed on Mar. 11, 2013.

(51) Int. Cl.
*A61N 2/00* (2006.01)
*A61N 2/02* (2006.01)

(52) U.S. Cl.
CPC ............ *A61N 2/008* (2013.01); *A61N 2/006* (2013.01); *A61N 2/02* (2013.01)

(58) Field of Classification Search
CPC .......... A61N 2/006; A61N 2/008; A61N 2/02
See application file for complete search history.

(56) References Cited

U.S. PATENT DOCUMENTS 6,117,066 A    12/2000   Abrams et al.
6,561,968 B1 *   5/2003   Dissing .................... A61N 2/02
                                                          600/13

(Continued)

OTHER PUBLICATIONS

International Search Report for PCT/US2014/023808, dated Aug. 29, 2014, 3 pages.

(Continued)

*Primary Examiner* — Christine H Matthews
(74) *Attorney, Agent, or Firm* — Eleanor Musick; Scott Davison; Musick Davison LLP

(57) ABSTRACT

A device and method are provided for treatment of peripheral nerve pain using a tMS stimulator for directing a low frequency, focused magnetic flux to a treatment area. A control module in wired and powered communication with the tMS stimulator, and a portable electronic device in wireless communication with the control module receive, generate and transmit feedback and control settings relating to a treatment parameters. The tMS stimulator may be configured in different sizes and shapes to provide varying pulse and magnetic field strengths. Guidance tools and measurement sensors may be provided to aid in positioning and directing the magnetic flux.

13 Claims, 18 Drawing Sheets

(56) References Cited

U.S. PATENT DOCUMENTS

| | | | |
|---|---|---|---|
| 8,376,925 B1 | 2/2013 | Dennis et al. | |
| 2003/0028072 A1* | 2/2003 | Fischell | A61N 1/32 600/13 |
| 2004/0122281 A1* | 6/2004 | Fischell | A61N 2/02 600/13 |
| 2005/0267355 A1 | 1/2005 | Parker | |
| 2007/0208249 A1 | 9/2007 | Kumar | |
| 2009/0203954 A1 | 8/2009 | Gronemeyer et al. | |
| 2010/0069704 A1* | 3/2010 | Peterchev | A61N 2/02 600/14 |
| 2010/0185042 A1* | 7/2010 | Schneider | A61N 2/004 600/13 |
| 2010/0210894 A1* | 8/2010 | Pascual-Leone | A61N 2/02 600/14 |
| 2011/0009736 A1* | 1/2011 | Maltz | A61N 5/1049 600/424 |
| 2012/0184801 A1 | 7/2012 | Simon et al. | |
| 2012/0197064 A1* | 8/2012 | Hwang | A61N 2/02 600/13 |
| 2012/0203054 A1 | 8/2012 | Riehl et al. | |
| 2014/0235929 A1* | 8/2014 | Rohan | A61N 1/40 600/14 |
| 2015/0018667 A1* | 1/2015 | Radman | A61N 1/20 600/411 |

OTHER PUBLICATIONS

Kobayashi et al., "Transcranial magnetic stimulation in neurology", The Lancet, Neurology vol. 2 Mar. 2003, pp. 145-154.

Leung et al., "Effect of Low Frequency Transcutaneous Magnetic Stimulation on Sensory and Motor Transmission," Bioelectromagnetics, 2015, pp. 1-10.

Leung et al., "Transcutaneous Magnetic Stimulation (tMS) in Alleviating Post-Traumatic Peripheral Neuropathic Pain States: A Case Series," Pain Medicine 2014; 15: 1196-1199.

Marlow, et al. "Efficacy of Transcranial Direct Current Stimulation and Repetitive Transcranial Magnetic Stimulation for Treating Fibromyalgia Syndrome: A Systematic Review," Pain Practice, May 2012.

* cited by examiner

| Patient | Age | Gender | Site of Neuroma or Nerve Entrapment | Number of tMS sessions | Frequency of tMS (hz) | Total number of pulses per session | Pre-treatment NRS Score | Pre-treatment Allodynia | Post-treatment NRS Score | Post-treatment Allodynia | % of Pain Reduction |
|---|---|---|---|---|---|---|---|---|---|---|---|
| 1 | 62 | M | Left Groin | 4 | 0.5 | 400 | 7 | Y | 0.0 | N | 100 |
| 2 | 41 | F | Right foot | 3 | 0.5 | 400 | 5 | N | 0.0 | N | 100 |
| 3 | 51 | F | Abdominal Wall | 4 | 0.5 | 400 | 5 | Y | 2.0 | N | 60 |
| 4 | 56 | M | Left elbow | 3 | 0.5 | 400 | 3 | N | 0.0 | N | 100 |
| 5 | 25 | M | Left Groin | 3 | 0.5 | 400 | 5 | Y | 2.0 | N | 60 |
| Average | 47 | | | 3.4 | 0.5 | 400 | 5 | | 0.8 | | 84 |

Table 1. Summary of patients' pain condition, tMS treatment setting and outcome. tMS: Transcutaneous Magnetic Stimulation; NRS: Numerical Rating Pain Scale

FIG. 11

PORTABLE TRANSCUTANEOUS MAGNETIC STIMULATOR AND SYSTEMS AND METHODS OF USE THEREOF

RELATED APPLICATIONS

This application is a 371 national stage filing of International Application No. PCT/US2014/023808, filed Mar. 11, 2014, which claims the benefit of U.S. Provisional Application No. 61/776,050, filed Mar. 11, 2013, the contents of which are incorporated herein by reference in its entirety.

FIELD OF THE INVENTION

The present invention relates to a device, system and method for non-invasive and self-administered treatment of peripheral pain, and more particularly to a portable device, system and method for transcutaneous magnetic stimulation (tMS).

BACKGROUND OF THE INVENTION

Peripheral nerve injury may result in the development of chronic intractable pain. Some patients prove unresponsive to conservative pain management techniques. Peripheral Nerve Stimulation (PNS) has developed as a successful therapy for pain management when the pain is known to result from a specific nerve. PNS is based in part on the Melzack-Wall gate control theory of pain. Sweet and Wespic first used electrical stimulation of peripheral nerves in the 1960s to mask the sensation of pain with a tingling sensation (paresthesia) caused by the electrical stimulation. Subsequent refinements in the technology, surgical technique and patient selection have led to improved long term results.

Efforts have been made to treat psychiatric disorders with peripheral/cranial nerve stimulation. Recently, partial benefits with vagus nerve stimulation in patients with depression have been described in U.S. Pat. No. 5,299,569. Another example of electrical stimulation to treat depression is described in U.S. Pat. No. 5,470,846, which discloses the use of transcranial pulsed magnetic fields to treat depression. Yet further, U.S. Pat. No. 5,263,480 describes that stimulation of the vagus nerve may control depression and compulsive eating disorders and U.S. Pat. No. 5,540,734 teaches stimulation of the trigeminal or glossopharyngeal nerves for psychiatric illness, such as depression.

Another example of peripheral nerve stimulations include, for example, stimulating the C2 dermatome area to treat occipital neuralgia, which may be defined generally as an intractable headache originating in the back of the head in the vicinity of the C2 dermatome area (U.S. Pat. No. 6,505,075). This method of delivering electrical stimulation energy to the C2 dermatome area to treat occipital neuralgia involves positioning stimulation electrodes of an implantable electrical stimulation lead with at least one electrode in the fascia superior to in a subcutaneous region proximate the C2 dermatome area.

Yet further, the use of electrical stimulation for treating neurological diseases, including such disorders as movement disorders including Parkinson's disease, essential tremor, dystonia, and chronic pain, have also been widely discussed in the literature. It has been recognized that electrical stimulation holds significant advantages over lesioning since lesioning destroys the nervous system tissue. In many instances, the preferred effect is to modulate neuronal activity. Electrical stimulation permits such modulation of the target neural structures and, equally importantly, does not require the destruction of nervous tissue. Such direct electrical stimulation procedures include electroconvulsive therapy (ECT), transcranial direct current stimulation (tDCS) and vagal nerve stimulation (VNS). In addition, indirect cortical (brain) electrical stimulation can be achieved via transcranial magnetic stimulation (TMS).

Traditional treatment options, for some forms of intractable pain (occipital pain, traumatic brain injury) that have proven to be resistant to medications, usually involve chemical, thermal or surgical ablation procedures following diagnostic local anesthetic blockade. Surgical approaches include neurolysis or nerve sectioning of either the C2 dermatome area in the occipital scalp or at the upper cervical dorsal root exit zone (extradural). Foraminal decompressions of C2 roots as well as C2 ganglionectomy have also been effective in reported cases.

Transcranial magnetic stimulation (TMS) was first introduced in 1985. TMS provided a non-invasive, safe and painless method of activating the human motor cortex and assessing the integrity of the central motor pathways. Since its introduction, the use of TMS in clinical neurophysiology, neurology, neuroscience, and psychiatry has spread widely.

TMS is based on the principle of electromagnetic inductions. If a pulse of current passing through a coil placed over a person's head has sufficient strength and short enough duration, rapidly changing magnetic pulses are generated that penetrate scalp and skull to reach the brain with negligible attenuation. These pulses induce a secondary ionic current in the brain. The site of stimulation of a nerve fiber is the point along its length at which sufficient current to cause depolarization passes through its membrane. Depending on the stimulation setting, single stimuli can either excite or inhibit neuronal functions.

Magnetic stimulation provides a non-invasive method for modulating nerve function and chronic pain management. Current methods of magnetic treatment for pain can be delivered via either static or dynamic magnetic field. While the efficacy of static magnetic field treatment such as magnetic bracelets has yet to be substantiated, studies involving the use of repetitive transcranial magnetic stimulation (dynamic magnetic flux) have yielded appreciable evidence support the merits of the device in relieving pain. Aside from stimulating the brain, the utilization of dynamic magnetic flux in transcutaneous stimulation for pain relief has not been fully explored. This under-utilization is the result of a number of issues: 1) the current commercially-available magnetic stimulators are physically very bulky; 2) the coils usually require additional cooling units to prevent overheating; 3) the devices are too expensive to be accessible to the general public; and 4) operating the device requires special training and clinical privilege. These physical limitations, cost and the requirement of special training restrict the current scope of use of this non-invasive means of pain management outside of healthcare facilities.

Accordingly, the need remains for a device that is affordable and easy to use that makes tMS, an effective tool for management of chronic pain, readily available.

SUMMARY

Embodiments described herein include a transcutaneous magnetic stimulation (tMS) device that includes a tMS stimulator, a control module in wired and powered communication with the tMS stimulator, and a portable electronic device in wireless communication with the control module to receive, generate and transmit feedback and control settings relating to a treatment session. The tMS stimulator may be a flexible figure-of-eight coil configured in different sizes and shapes to provide varying pulse and magnetic field strengths for mobile, home or clinical uses, and also include guidance tools and measurement sensors to aid in positioning and directing the tMS stimulator to a target area for treatment.

In one embodiment, a transcutaneous magnetic stimulation (tMS) device comprises a tMS stimulator configured to deliver a magnetic pulse with at least one insulated magnetic coil; and a control module in powered communication with the tMS stimulator configured to control a pulse rate and magnetic field of the tMS stimulator.

In another embodiment, a method of treating a patient using transcutaneous magnetic stimulation (tMS) comprises the steps of configuring a control module to deliver a specified pulse rate and magnetic strength with a tMS stimulator; positioning the tMS stimulator over a target area of a human body; and delivering a magnetic pulse at the specified pulse rate and magnetic strength using the tMS stimulator.

In a further embodiment, a system for delivering a transcutaneous magnetic stimulation (tMS) therapy comprises a tMS device including a tMS stimulator and control module configured to deliver a magnetic pulse; a portable electronic device in wireless communication with the tMS device and configured to receive data from the control module relating to the delivered magnetic pulse and feedback from a user relating to the delivered magnetic pulse and their rating of pain at the treatment site; and a remote server in communication with the portable electronic device configured to receive the data from the control module relating to the delivered magnetic pulse and the feedback from the user relating to the delivered magnetic pulse.

BRIEF DESCRIPTION OF THE DRAWINGS

FIG. 11 is a table illustrating an amount of pain reduction experienced by patients with neuroma or post-traumatic neuropathic pain states after treatment with the tMS.

DETAILED DESCRIPTION

Described herein is a transcutaneous magnetic stimulator (tMS) device configured to modulate nerve function and reduce pain. The transcutaneous magnetic stimulation (tMS) device that includes a tMS stimulator, a control module in wired and powered communication with the tMS stimulator, and a portable electronic device in wireless communication with the control module to receive, generate and transmit feedback and control settings relating to a treatment session. The tMS stimulator may be a flexible figure-of-eight coil configured in different sizes and shapes to provide varying pulse and magnetic field strengths for mobile, home or clinical uses, and also include guidance tools and measurement sensors to aid in positioning and directing the tMS stimulator to a target area for treatment.

I. Transcutaneous Magnetic Stimulator Device

Figure 1:
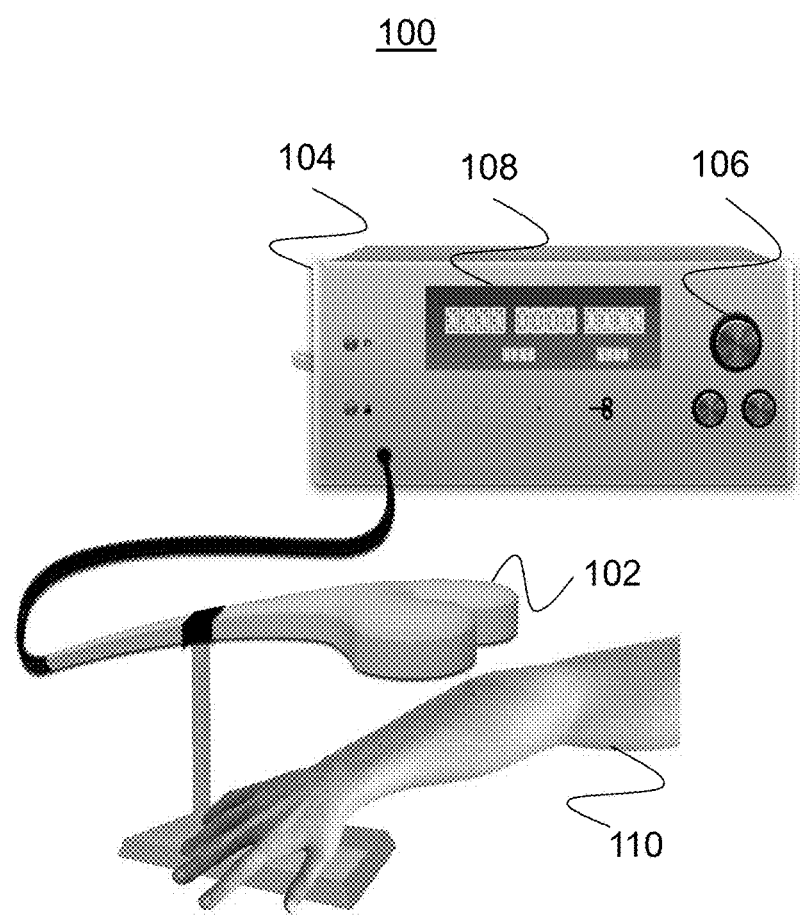
FIG. 1 is an illustration of a transcutaneous magnetic stimulator (tMS), according to one embodiment of the invention.

FIG. 1 illustrates one embodiment of a tMS device 100, including a tMS stimulator 102 connected with a control module 104. The control module 104 may include one or more selection knobs 106 to adjust the various settings of the tMS stimulator and a display screen 108 to display the settings, status and other indicators. The tMS stimulator 102 may be positioned over a portion of a human body 110, animal or other living tissue where the magnetic stimulation is then applied.

tMS Stimulator

The tMS stimulator 102 produces small electrical currents around a neuroma or nerve entrapment without anesthetics, and may be an insulated coil which can be held over a target treatment area either with or without contacting the affected area. This method of pain neuromodulation provides a major advantage in treating patients with increased sensitivity to non-noxious stimuli (allodynia), as the treatment does not require direct device-patient contact or direct tissue penetration. When a current is passed around the coil, a dynamic magnetic flux will pass through the skin and into the first few centimeters of the skin without attenuation. In one embodiment, the coil is shaped into a figure-of-eight coil that gives a focused dynamic magnetic flux from the center of the coil to the target site which can be marked with an extended optical cross-hair in order to target a specific area on the body. This dynamic magnetic flux induced neuronal stimulation is far more focused than other direct current stimulation modalities such as a transcutaneous electrical nerves stimulator (TENS).

In one embodiment, the tMS stimulator 102 operates within a frequency range that is variable from approximately 0.2 Hz to 5 Hz. The frequency range may be divided into a low frequency stimulation range from approximately 0.2 Hz-1 Hz and a high frequency range from approximately 1 Hz to 5 Hz. The magnetic pulse field strength has a continuous stimulation capacity of up to 3 Tesla. A biphasic waveform is more effective with regard to threshold of excitation and response amplitude when compared to a traditional monophasic waveform. In one embodiment (see FIG. 3G), a magnetic core of permalloy, Mu-metal, or other ferromagnetic compound may be assembled in the center of the coil to further increase the strength of the magnetic flux. In one embodiment, the magnetic core allows for a decrease in the current needed to effectuate a treatment from approximately 1200V to 700V.

Figure 2:
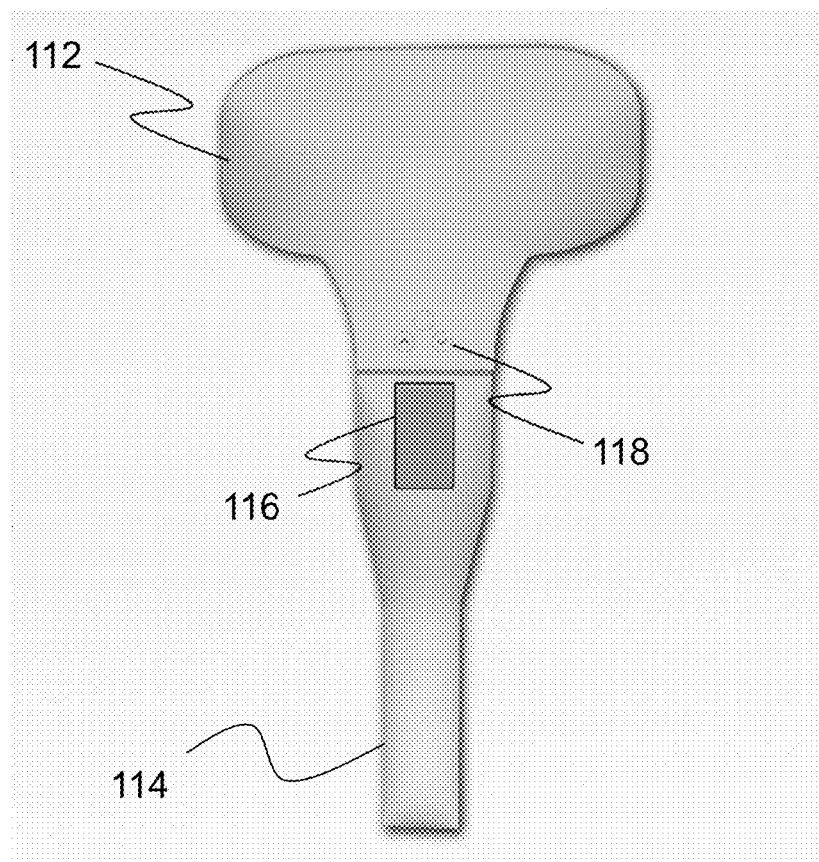
FIG. 2 is an illustration of a tMS stimulator, according to one embodiment of the invention.

One embodiment of a tMS stimulator 102 is illustrated in FIG. 2, with further illustrations of the coil housing illustrated in FIGS. 3A-3G. In the embodiment of the stimulator 102 illustrated in FIG. 2, the tMS stimulator 102 includes a flexible figure-of-eight coil encased in a coil housing 112 that can either be handheld by a user or mounted to a base or other mounting device at a handle portion 114. In one embodiment, the coil housing 112 measures approximately 5 inches in length, approximately 2.5 inches wide and approximately 1.5 inches deep. The handle portion 114 of the tMS stimulator may extend approximately 7.5 inches from the coil portion and allow for the tMS stimulator to be handheld or mounted during use. The tMS stimulator 102 may also include a tMS display screen 116 to display information on the positioning and treatment, such as a tracking distance to a target region or treatment parameters related to the tMS settings. The tMS stimulator 102 may also include control buttons 118 for controlling the settings and other parameters of the tMS stimulator. The display screen 116 and the buttons 118 may be capacitive touch or capable of receiving other touch inputs.

Figure 3A:
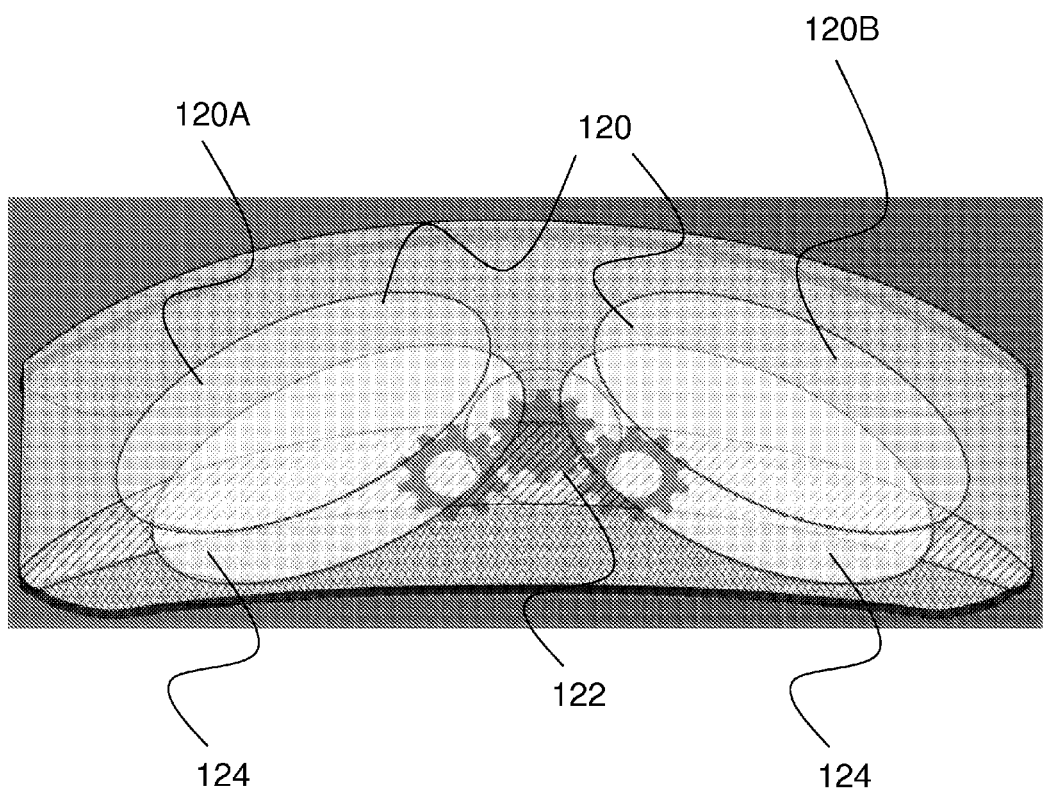
FIGS. 3A-3G are illustrations of a figure-of-eight coil within the tMS stimulator and a coil rotation mechanism, according to one embodiment of the invention.
Figure 3B:
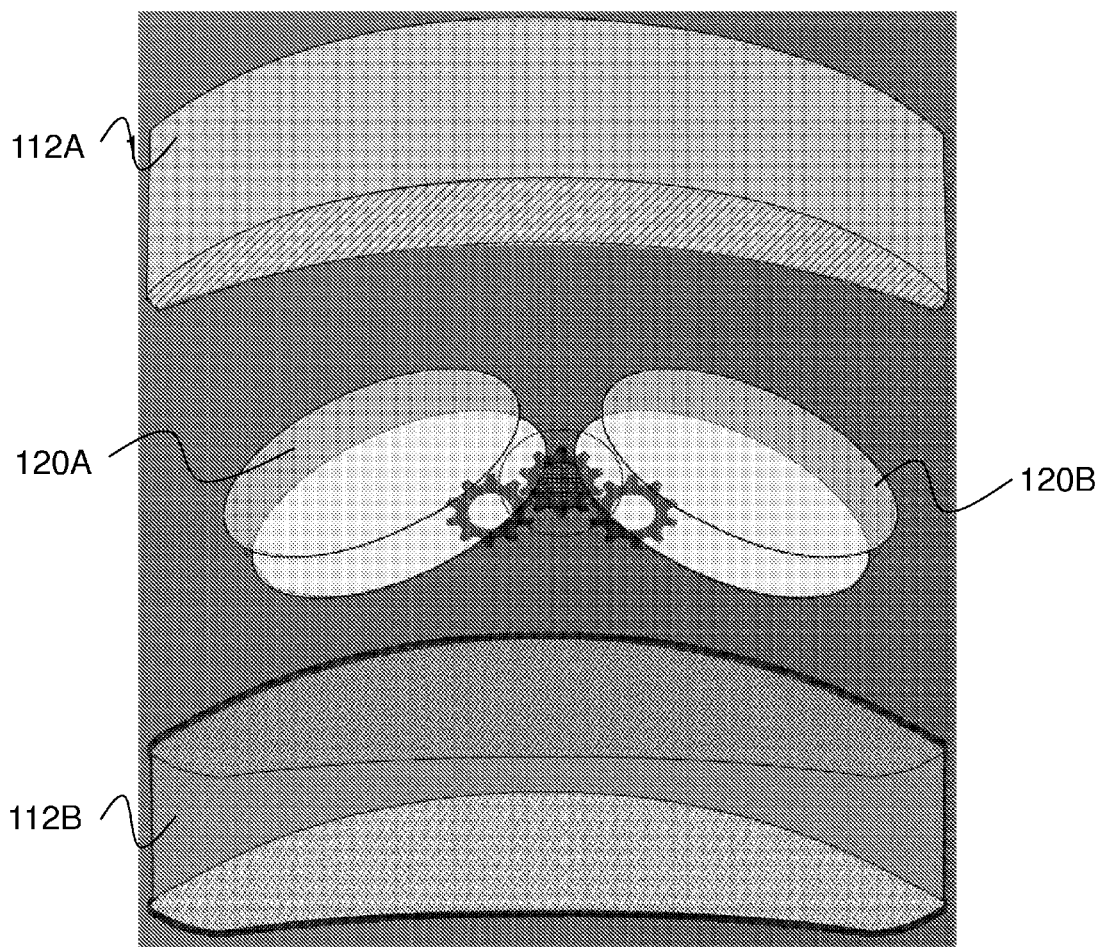

A transparent illustration of the coil housing 112 is illustrated in FIG. 3A, showing the configuration of the figure-of-eight coil 120 with a left coil 120A and right coil 120B. In one embodiment, the figure-of-eight coil 120 may rotate internally up to approximately 30 degrees in order to adjust a focal point of the treatment by redirecting the magnetic field. The focal point may be focused to within approximately 3-5 millimeters in the rotated configuration of FIG. 3A. FIG. 3A illustrates a rotated configuration of the figure-of-eight coil 120, which is rotated via a central gear mechanism 122 attached to a curved mounting piece 124 (see FIG. 3C). FIG. 3B is an exploded view illustration of the coil housing 112, illustrating a top housing portion 112A and a bottom housing portion 112B which are fitted around the left coil 120A and right coil 120B.

Figure 3C:
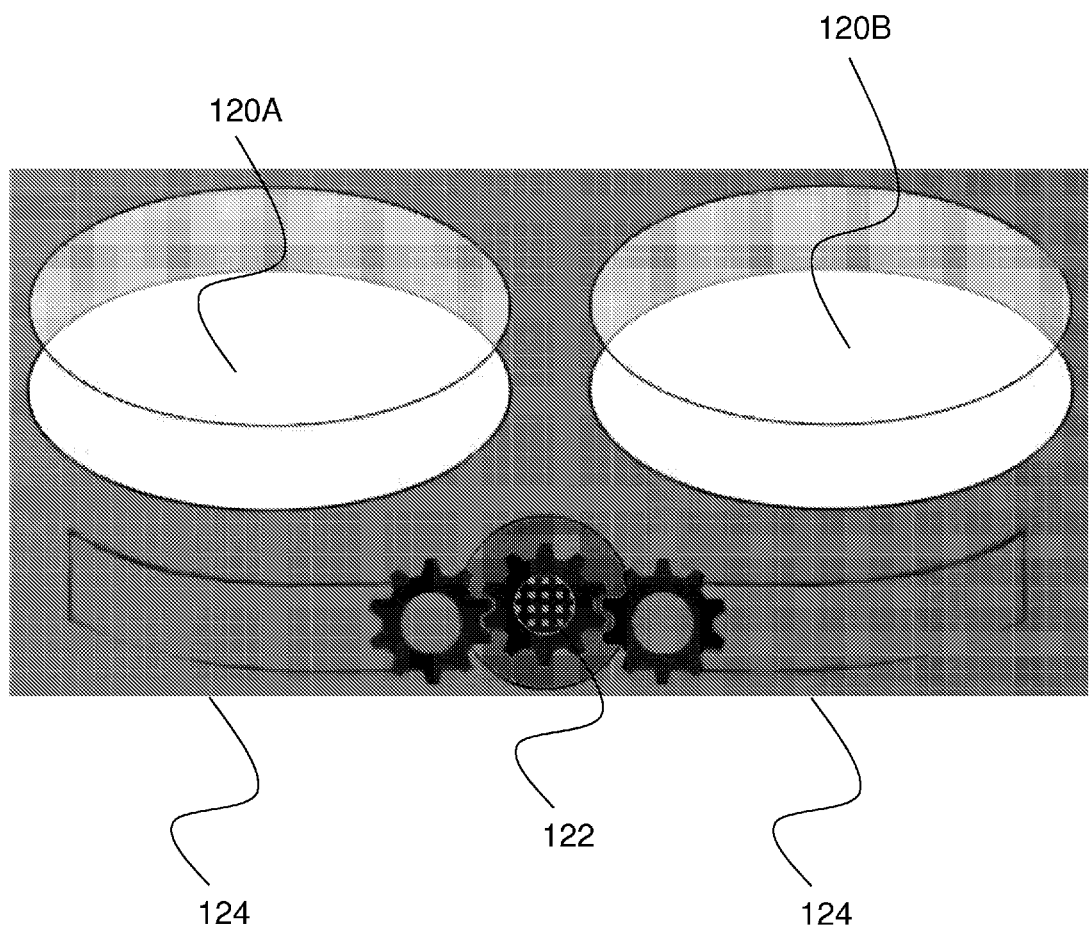
Figure 3D:
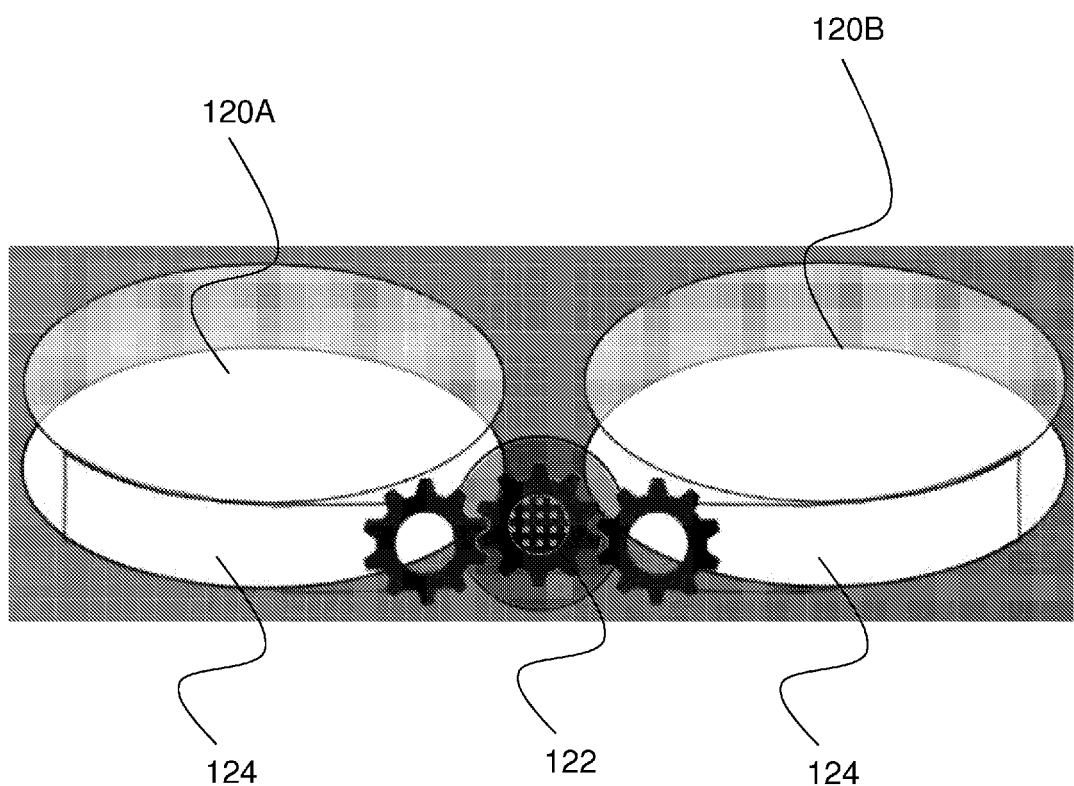

FIG. 3C is an exploded view illustration of the figure-of-eight coil 120 separated from the gear mechanism 122 and curved mounting pieces 124 simply for illustration purposes to show the shape and interaction of the gear mechanism 122 and curved mounting pieces 124 with the coil 120. FIG. 3D illustrates the gear mechanism 122 and curved mounting pieces 124 in communication with their respective coils 120A and 120B in an un-rotated configuration.

Figure 3E:
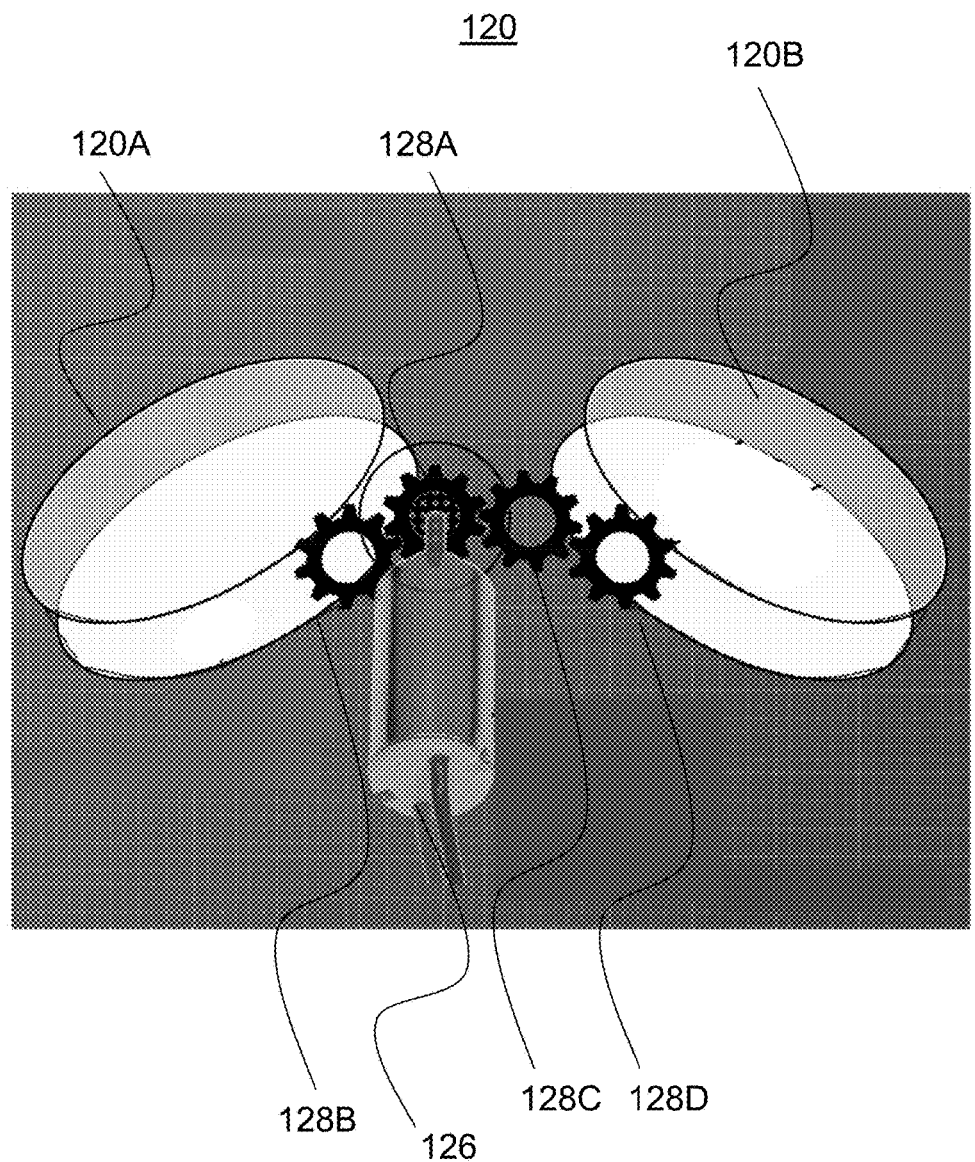
Figure 3F:
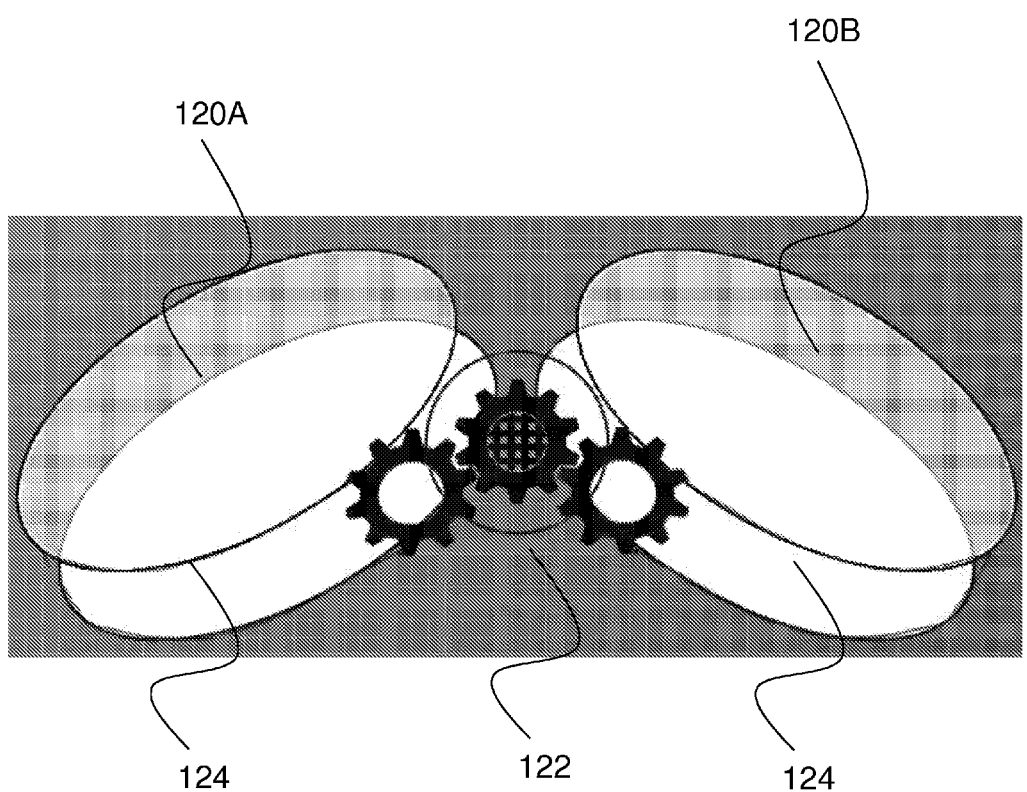

FIG. 3E illustrates the mechanics of the gear mechanism 122, which may be driven by a small motor 126 attached with a central gear 128A. One of the coils 120A may be connected with the gear mechanism through a single secondary gear 128B, while the opposing coil 120B is connected with the gear mechanism through two secondary gears 128C and 128D in order to effectuate an opposite direction of rotation of the coils so that they both rotate inward to focus on a single target point. For simplicity of illustration only, the secondary gears 128C and 128D are not illustrated in other figures. FIG. 3F is an illustration of the figure-of-eight coil 120 in the rotated configuration after the motor 126 actuates the gears to rotate the coil 120 via the mounting pieces 124.

Figure 3G:
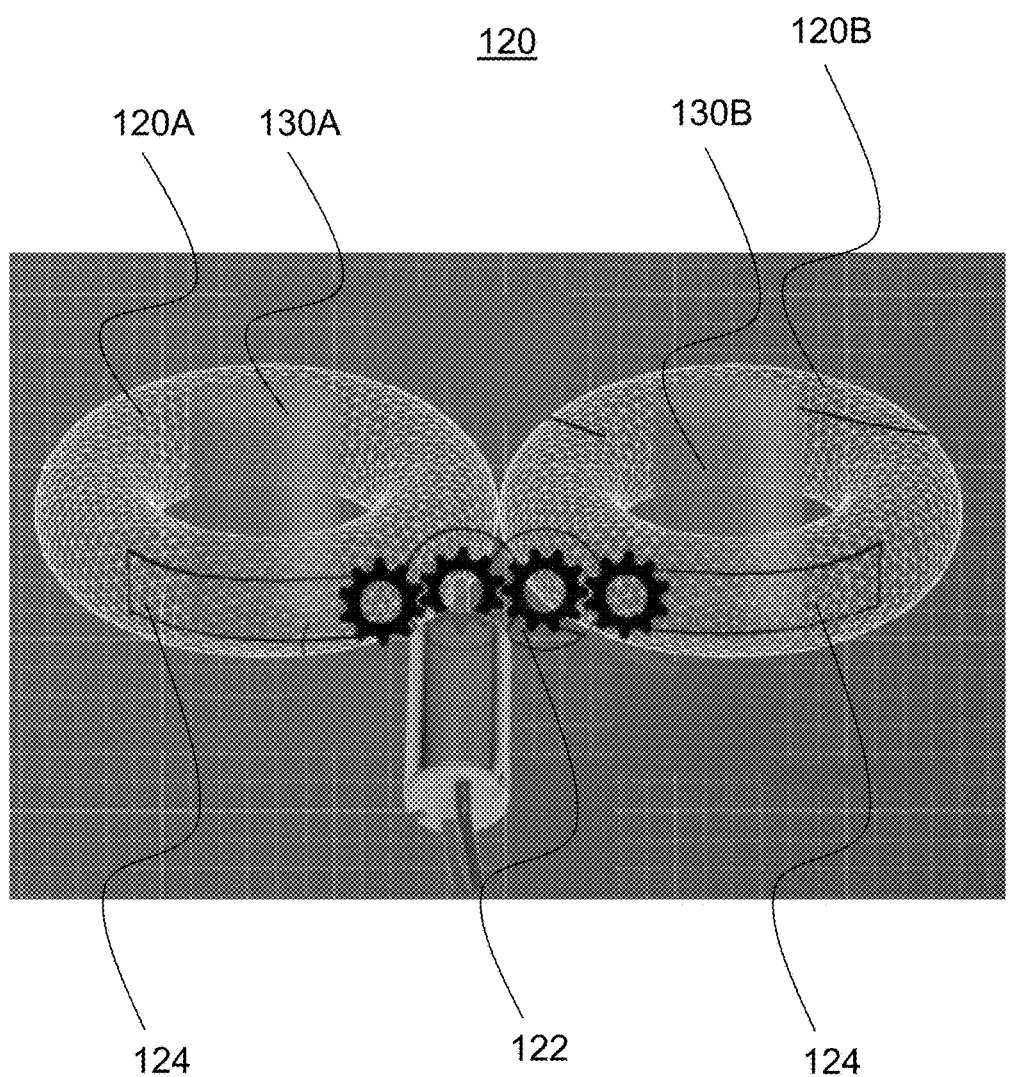

FIG. 3G is a three dimensional graphical illustration of one embodiment of the coil 120 with a respective magnetic core 130A and 130B disposed within each respective coil 120A and 120B, as described above. The curved mounting pieces 124 are also more clearly shown disposed against an outer side wall of the coils 120. The curved mounting pieces may be metal pieces which are attached to the coils via screws or any other practical attachment means.

The tMS stimulator 102 may also include a light source (not shown) such as an LED on an application side of the coil portion that faces the body 110 to guide a center of magnetic flux generated by the coil to a target treatment area. An accelerometer may also be implemented in the tMS stimulator 102 to detect magnitude and direction of the probe acceleration to sense orientation, vibration, shock and falling in order to turn off the device during deviations from treatment locale.

A magnetometer may also be included to measure the strength and direction of magnetic fields generated by the stimulation coils to optimize accuracy and intensity of treatments. Further, a proximity sensor may be included to detect and confirm that the target region of treatment is within the appropriate range of the tMS stimulator 102 to precisely deliver treatment to achieve the greatest results.

The tMS stimulator 102 may be designed with a thermode to automatically shut off the stimulation probe in the the event of overheating from both internal and external factors. For efficiency, controller software in the control module 104 may utilize a negative-feedback method and detect unusual heating patterns to prevent damage to the device, or injury to the user, by warning the user and turning off the device.

In one embodiment, guidance for proper positioning of the target region can be provided by a combination of marks applied to the user's skin, preferably using a safe marking material that is invisible or nearly-invisible under normal light conditions. For example, the ink can be fluorescent visible only under focused UV light, e.g., a black light. The device may include a UV light source that is optically focused to coincide with the optimal flux location from the stimulation probe. In a preferred embodiment, the UV light source may be an LED that produces light at around 400 nm, making it more compact, rugged and easily portable, while generating light that is near the lower end of UV wavelengths and, therefore, safer for repeated exposure.

Control Module

Figure 4:
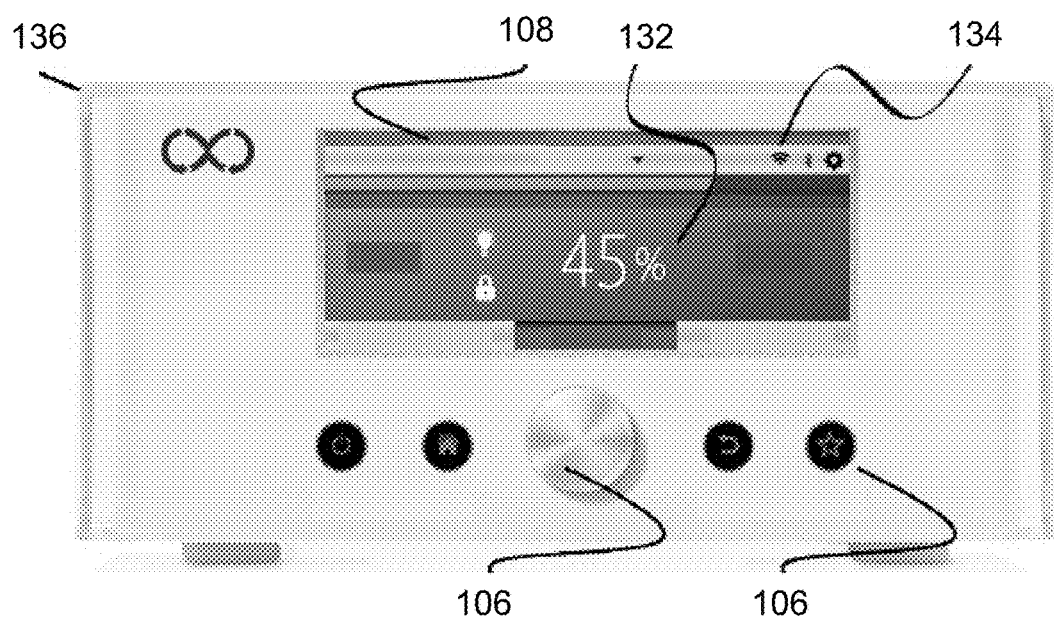
FIG. 4 is an illustration of a control module for the tMS stimulator device, according to one embodiment of the invention.

The control module 104 is configured with hardware and software to precisely control the tMS stimulator 102 and provide data relating to the treatment in real-time and post-treatment. One embodiment of the control module 104 is illustrated in further detail in FIG. 4. Although the control module 104 is illustrated with one or more control knobs 106 to adjust the tMS stimulator settings, a touchscreen display 108 may instead be used to eliminate the need for physical control buttons. The touchscreen display may present tMS stimulator information 132 or connection status indications 134 pertaining to connections with the portable electronic device or another network device. In one embodiment, the control module 104 may be equipped with a handle (not shown) for portability and powered by AC electricity or a battery. The control module may be formed with a thermoplastic housing 136 to isolate a user from the high-voltage components inside. In one embodiment, the control module 104 may be equipped with rechargeable batteries (Lithium-ion & Sodium-ion) or graphene supercapacitors to increase mobility. The control module 104 displays the pulse width, amplitude and frequency of the treatment, which can be adjusted via one or more separate control knobs. The output of the device is 3 T at 1 Hz, with 20 kTesla/sec. instantaneous flux.

The control module 104 may also include a wireless transmitter/receiver and corresponding software to provide a wireless connection with another device, for communication, tracking and management of treatment, remotely programming treatment parameters, troubleshooting assistance, updating software and to ensure compliance. In an exemplary embodiment, low energy BLUETOOTH® 4.0 technology provides connection to a mobile device, e.g., a smart phone or tablet computer, for tracking and managing treatment and results to optimize therapeutic parameters and maximize analgesic efficacy.

Figures 5A, 5B, 5C:
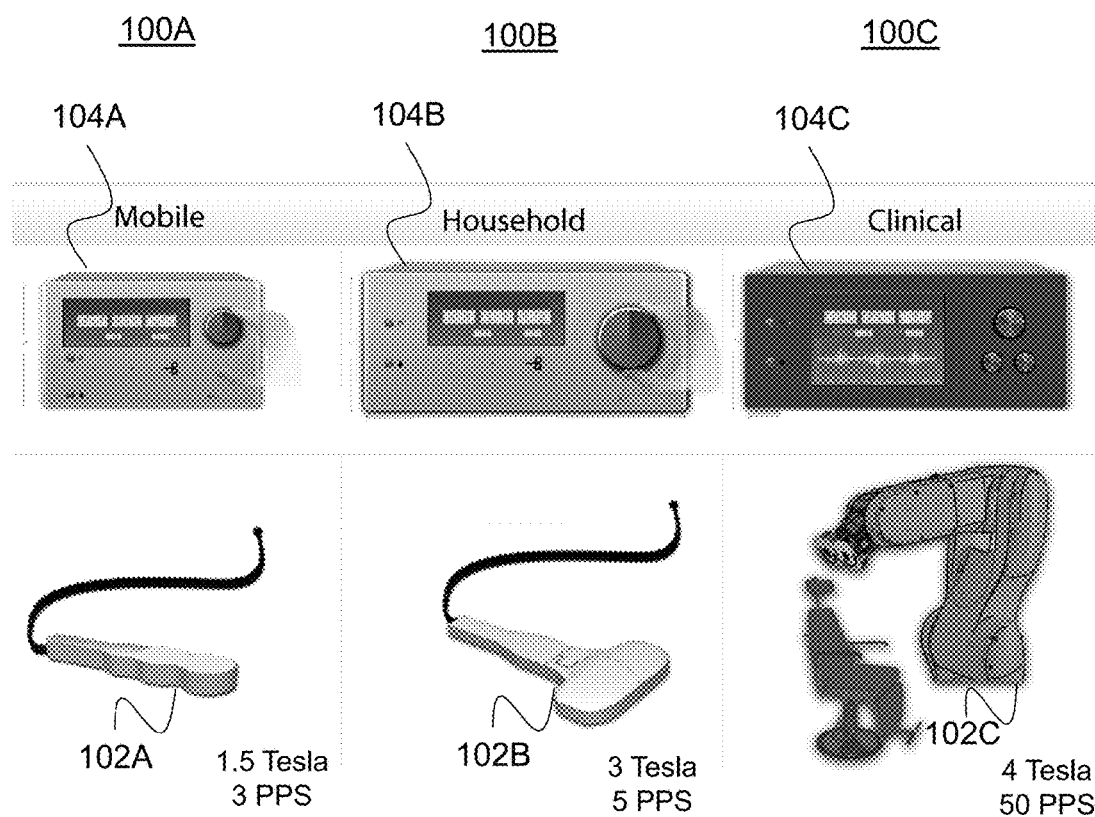
FIGS. 5A-5C illustrate alternative configurations of the tMS, according to one embodiment of the invention.

FIGS. 5A-5C illustrate alternative embodiments of the tMS device 100 designed for different applications. FIG. 5A illustrates a mobile tMS device 100A with a portable control module 104A and tMS stimulator 102A which provide a reduced output of approximately 1.5 Tesla and 3 pulses per second (PPS). FIG. 5B illustrates a larger tMS device 100B with a larger control module 104B and tMS stimulator 102B configured for in-home use that provides approximately 3 Tesla and 5 PPS. A clinical tMS device 100C is provided in FIG. 5C, and illustrates a control module 104C with a larger display screen capable of displaying real-time signal data on the applied fields, as well as a tMS stimulator 102C mounted to a floor-mounted positioning arm that can be used to precisely direct treatment to a particular part of the body for a user sitting in a treatment chair. In one embodiment, the clinical tMS device 100C may be capable of outputting approximately 4 Tesla and 50 PPS.

Figure 6:
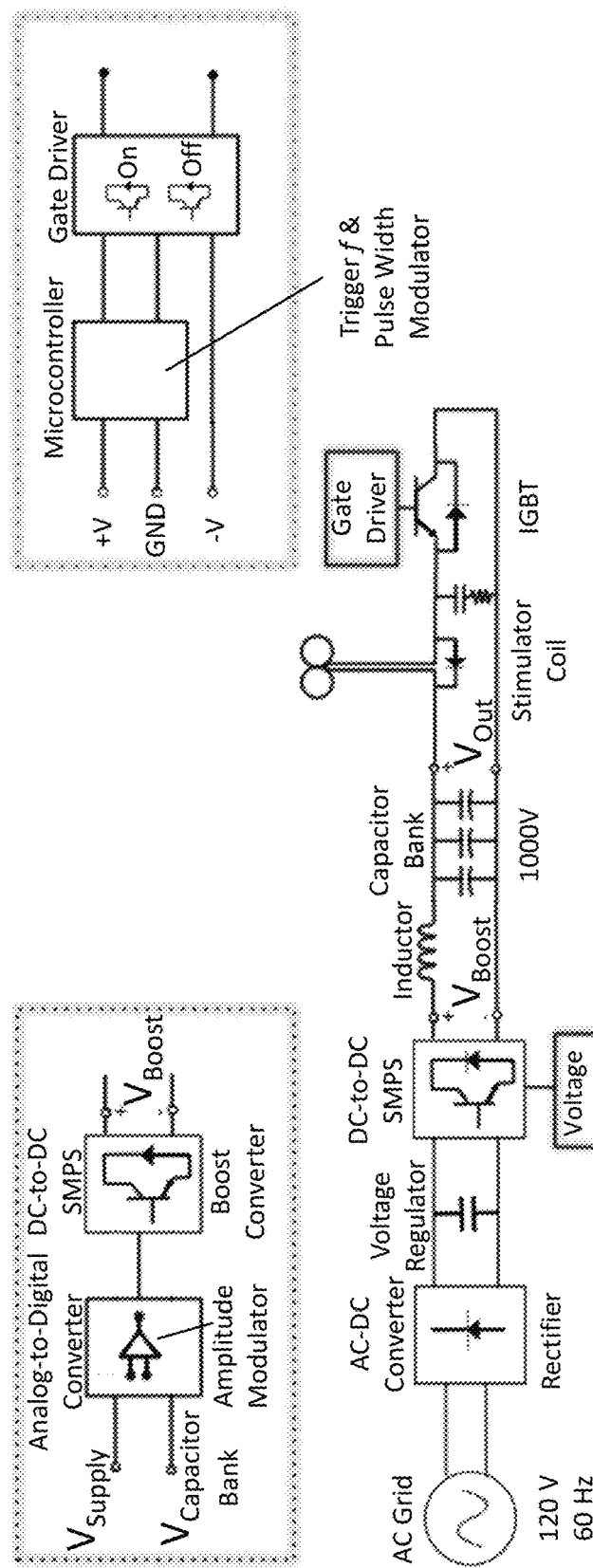
FIG. 6 is an exemplary circuit diagram for carrying out the functions of the tMS, according to one embodiment of the invention.

FIG. 6 illustrates the circuit design for operating the tMS device 100. The circuitry has been built to continuously monitor and adjust power outputs to ensure efficacy of the treatment and safety of the user. Crucial circuit components are tested in every power cycle, before and after each treatment administration with the primary hardware supervisory circuits and secondary software monitoring systems in communication with the Microcontroller unit. The circuitry boots in stages and if a failure is detected, safety interrupts will discontinue the booting process, shutdown device operation, and ask for servicing. The circuitry inside the control module 104 may also include parallel high voltage chargers, each capable of up to 1600 watt power output, energizing capacitor banks, with up to 2200 uF energy storage capacity, and discharging hardware to decrease loss of performance and increase reliability. The capacitor bank inside control module 104 may range in voltages from –2000 to +4500 volts DC in order to conserve energy and optimize performance. The maximum repetitive controllable on-state current within the control module and stimulation coil may reach up to 4000 volts DC. In one embodiment, multiple high power converting thyristors may be stacked to achieve the performance requirements of this pulsed power application. Heat from inductance may be managed internally with small, electrically powered, forced-air cooling systems utilizing continuous duty DC blower fans operating at up to 5200 RPM.

In one embodiment, the tMS system can be password- or biometrically-protected to ensure access only by approved users of the device.

II. Portable Electronic Device

In one embodiment, a portable electronic device may be utilized with the tMS to provide for wireless control of the tMS device and analysis of treatments. The portable electronic device may be a portable computing device such as a smartphone, tablet, laptop or wearable device that is configured to wirelessly communicate with the tMS, provide a visual interface for displaying information about the control of the tMS and treatments performed, and inputs (such as a touchscreen) for the user to interact with the portable electronic device. The portable electronic device may be connected with the tMS via a wireless connection protocol such as Bluetooth®, Wi-Fi®, NFC, or a proprietary device-specific network such as the 2net™ Platform® for wireless health, although the list should not be limited thereto. In one embodiment, an internal modem with an omnidirectional antenna may be utilized to connect with IEEE 802.16 family wireless hotspots and 3G telecommunications networks such as WiMAX. These networks may be utilized to passively transmit usage data on the device to a remote server for monitoring the usage and performance of the device. Updates to the settings, programs and configuration of the hardware, software and firmware may be provided over these networks, whether by a technician who is improving the performance of the device or by a physician updating a patient's treatment session parameters. A wireless network connection may also be utilized for tracking the device if lost or stolen.

Figures 7A, 7B, 7C:
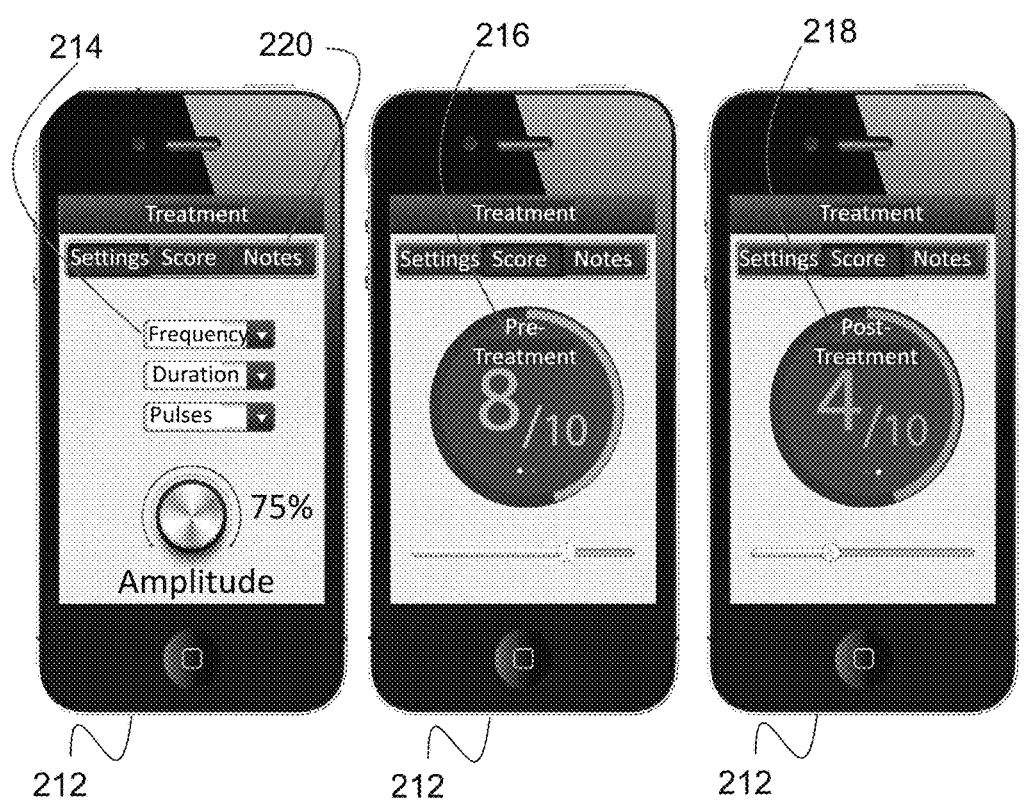
FIGS. 7A-7C illustrate graphical user interfaces on a portable electronic device configured to communicate with the tMS, according to one embodiment of the invention.

FIGS. 7A-7C illustrate graphical user interfaces (GUIs) that may be displayed on a touchscreen display of a smartphone 212 to allow the user to input the settings 214 for their treatments and provide a pre-treatment pain score 216 and post-treatment pain score 218. The scores can then be correlated with the input settings 214 to determine which tMS settings provide the best reduction in pain. Additional notes relating to the treatment may be entered by the user in a notes tab 220.

In FIG. 7A, the user can select the levels of their tMS settings 214, including frequency, duration, pulses and amplitude. The settings may also be automatically transmitted from the tMS before, during or after a treatment session so the user can instantly provide feedback related to the session. In one embodiment, this interface may also allow the user to control the tMS device for executing a treatment session. FIG. 7B illustrates a pain score interface where the user inputs a pre-treatment pain score 216, while FIG. 7C illustrates the interface where the patient inputs a post-treatment pain score 218. The differences between scores can then be compared with the settings 214 for the particular treatment to determine how effective the treatment was at the particular settings. The user may add notes 220 to further explain the reasons for the scores or other information relevant to the treatment, and these notes 220 may be transmitted to a healthcare professional along with the treatment settings and pain scores, as will be described in further detail below.

III. Systems for Monitoring Patient Progress

Figure 8:
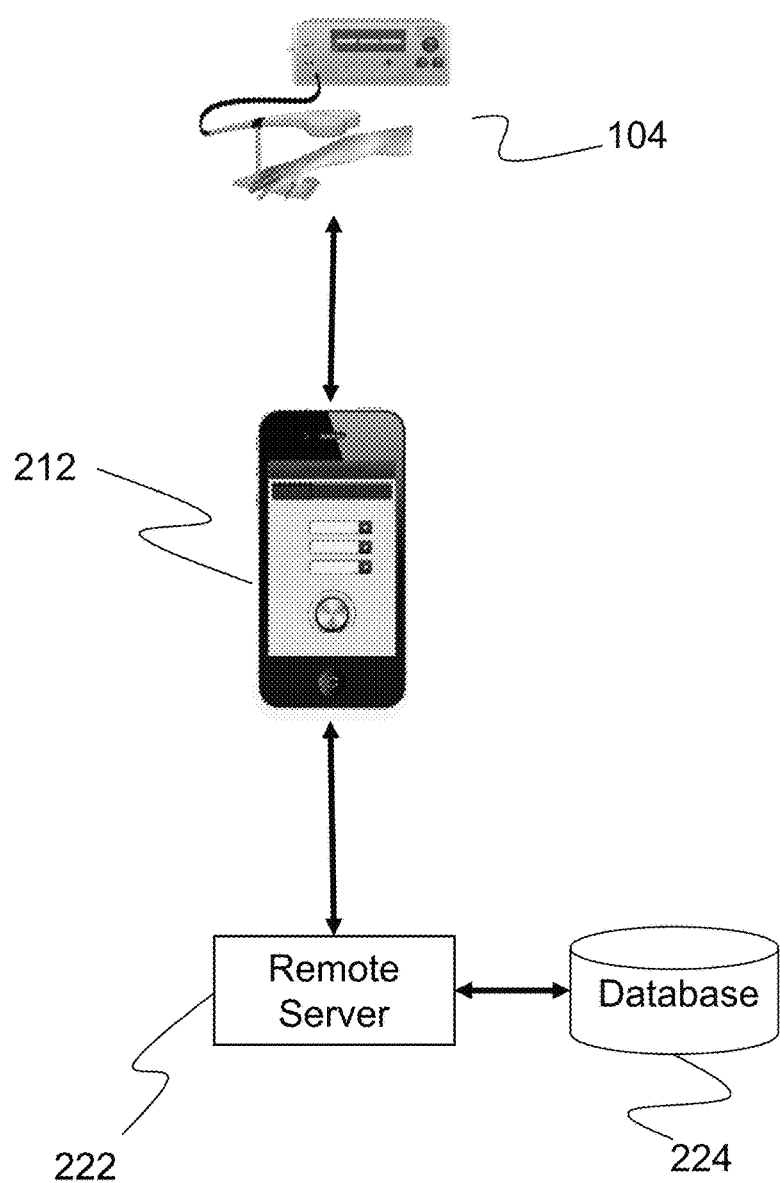
FIG. 8 is an illustration of a system for controlling and tracking treatments performed by the tMS, according to one embodiment of the invention.

A system for providing treatment using the tMS is illustrated in FIG. 8, where the the portable electronic device 212 is configured to communicate both with the tMS device 204 and with a remote server 222, where data related to the treatment sessions, user feedback, device settings, etc. can be transmitted for analysis at a remote location. The data received at the remote server may be stored in a database 224, where the data for individual users or a group of users may be analyzed to determine the effectiveness of treatments on certain types of pain, symptoms, body parts, etc. The remote server 222 may also be configured to transmit treatment settings to the portable electronic device 212, which can then be transmitted directly to the tMS in order to provide updated treatment plans and settings based on the user feedback, thus avoiding the need for the user to visit with a healthcare provider in person in order to update their treatment program.

IV. Exemplary Methods

Figure 9:
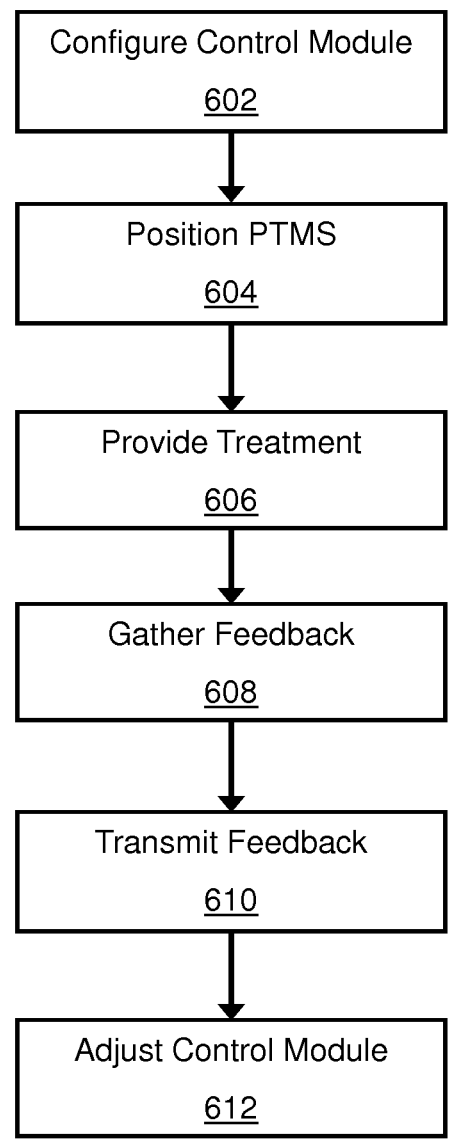
FIG. 9 illustrates a method of configuring, performing and tracking a tMS treatment, according to one embodiment of the invention.

An exemplary method of providing tMS is illustrated by the flow diagram in FIG. 9. In a first step 602, the control module is configured with the settings for a treatment session, including the frequency, duration, pulse and amplitude. The tMS stimulator is then positioned adjacent to a body part which has been identified for treatment in step 604, using any one or more of the positioning aids described above. Once the tMS stimulator is correctly positioned, the treatment session can be started (step 606). During and after the treatment session, feedback may be obtained (in step 608) from the control module or the user (via the portable electronic device) to ensure that the device is performing adequately and that the user is experiencing a decrease in pain. In step 610, the feedback may be transmitted to a remote location or stored locally for analysis by the user or a healthcare provider, and in step 612, the treatment plan or device settings may be adjusted as a result of the analysis.

V. Applications

Figure 10:
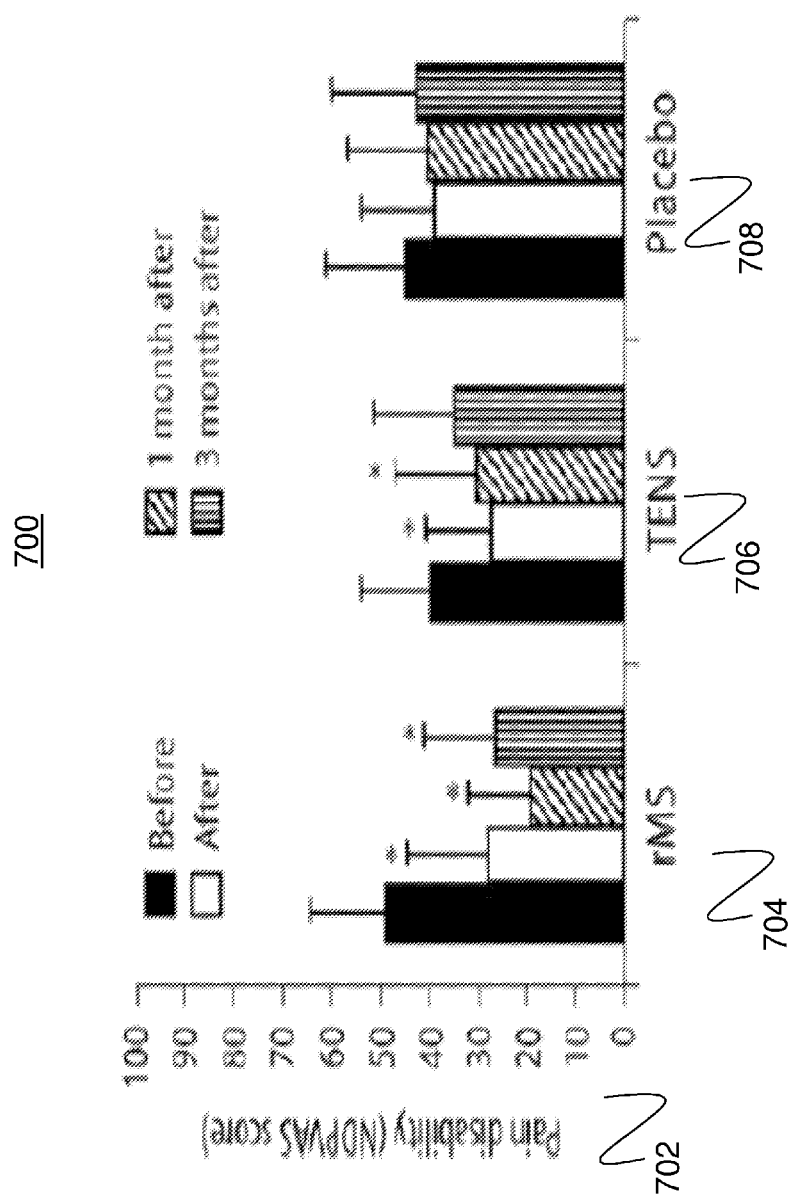
FIG. 10 is a graph illustrating comparative results from a study using tMS for treatment of myofacial pain.

The applications for the tMS device are numerous and not limited simply to basic physical pain sensations. In one embodiment, the device may be utilized for treatment of post-traumatic neuroma/nerve entrapment pain. In addition to treatment of neuroma, preliminary data for using tMS for treating myofacial pain is also available. Smania, et al. ("Repetitive magnetic stimulation: a novel therapeutic approach for myofacial pain syndrome", *J. Neurol.* 252(3): 307-314, 2005) published a study in 2005 documenting the result of tMS in comparison the TENS and placebo treatment. The result is summarized in FIG. 10, which shows changes 700 in the NDPVAS scale 702 in the rMS 704, TENS 706 and placebo groups 708. The asterisk indicates statistically significant differences. FIG. 11 is a table illustrating an amount of pain reduction experienced by patients after treatment with the tMS.

Additional applications include pre-local anesthetic/skin penetration analgesia, as injection of local anesthetic into peripheral tissue often induces unpleasant stinging and painful sensation for patients. Many practitioners deal with this discomfort by application of chloroethane ("freeze spray") during the injection; however, chloroethane has the drawbacks of being flammable and narcotic. The tMS device could provide significant benefit in clinical uses such as peripheral IV placement, dental procedures, pediatric procedures which require skin penetration, or any outpatient pain or non-pain related procedure.

In one embodiment, the device can be used as a self-administered non-invasive treatment for pain. The potential pain treatment/anesthesia application of the device includes: myofascial (muscle) pain, nerve entrapment pain, pain related to nerve injury, pain related to muscle injury, pain related to muscle fatigue, pain related to surgical incision, pain related to nerve sensitivity, pain related to neuropathic pain, surgical scar pain, neuroma pain, skin anesthesia in lieu of local anesthetics, skin anesthesia for any procedure requires skin penetration, surgical anesthesia prior to surgical incision, pain related to pre and post-dental procedure, pain related to inadequate blood circulation, minimizing pain prior to local anesthetic injection, minimize pain prior to any needle or instructmental skin penetration, physical therapy, occupational therapy and improving muscle or joint range of motion.

Recently the use of tMS has been shown to be beneficial in managing intractable central neuropathic states and headaches. tMS is also known to facilitate nerve repair/regeneration. While high frequency tMS(>1 Hz) results in neuronal excitation, low frequency tMS(<1 Hz) results in neuronal inhibition. Therefore, low frequency tMS can also be applied as a treatment option for managing a state of neuronal hypersensitivity known to exist in neuroma/nerve entrapment.

VI. Case Studies

Over twenty patients with pain due to peripheral nerve injury were treated with transcutaneous magnetic stimulation. 90% of these patients had failed medication and injection therapies. The overall long term pain reduction using the inventive system and method is about 80%, with a maintenance treatment given at a four-to-six week interval.

A case series summary describing the treatment outcome in 5 patients is described below. The five patients exhibited post-traumatic neuroma/nerve entrapment pain. Patients were selected based on their history of traumatic nerve injury, physical finding of neuroma with palpation near the site of injury, reproducible paresthesia in distribution of the injured nerve with palpation and prior history of inadequate pain relief with oral or topical analgesics, and local steroid and local anesthetics injection.

Low frequency (0.5 Hz) tMS was developed over the site of neuroma in five patients who have failed both steroid injection and conventional pain medications. 400 pulses of stimulation were delivered per treatment session. Each patient received 3-4 sessions of treatment over a period of two months. Pre and post intervention spontaneous pain levels were assessed with a numerical rating pain scale (NRS).

Average pre and post scores (±SD) on the NRS were 5.00 (±1.41) and 0.80 (±1.10) respectively, with an average pain reduction of 84% (±21.91) in the NRS after three to four treatments within two months. This analgesic effect appeared to be sustainable with repeated treatment delivered at a 6 to 8 week duration. Pre-treatment tactile allodynia found in three patients resolved after the initial 2 month treatment session.

The study demonstrates that tMS offers an innovative and non-invasive means of neuromodulation in managing peripheral neuropathic pain via dynamic magnetic flux.

Example 1

A 62 year old male patient presented with left groin pain. Patient had a history of inguinal hernia repair surgery 5 years prior to presentation. Pain was described as continuous, throbbing, worse with activity and at a level of 7 in a 0-10 Numerical Pain Rating Scale (NRS). Tactile allodynia to light stroking from a foam paint blush was present prior to the intervention. Patient was diagnosed with left groin neuroma based on physical examination finding of palpable neuroma (1.5 cm×1 cm) and paresthesia in the distribution of the genital branch of the left genitofemoral nerve. A CT scan showed no inguinal hernia recurrence. He had previously tried massage therapy, ibuprofen, naproxen, FLEXERIL®, and most recently DEPOMEDROL® and local anesthetic injections 4 times with minimal benefit. Subsequently local tMS therapy was initiated with frequency of 0.5 Hz and 75% amplitude and patient's pre-treatment and post-treatment levels were 4 and 0, respectively. Subsequently local tMS therapy was initiated at 0.5 Hz. 400 pulses were delivered over the site of the neuroma with each treatment. After 4 sessions of tMS treatment over a period of two months, his spontaneous pain level decreased to 0/10 NRS. He was treated at intervals ranging from 2 to 4 weeks with improvement noted in pain scores consistently both immediate and few weeks post-treatment. His tactile allodynia resolved, and he remained pain free with maintenance treatment at the same setting every 8 weeks.

Example 2

A 41 year old female initially presented to clinic for botulism toxin injections for chronic migraine treatment but was found to have chronic pain in right foot from plantar nerve entrapment. A neuroma (0.5 cm×0.5 cm) was identified with palpation on physical examination. With deep palpation over the neuroma, the pattern of paresthesia was reproducible along the medial plantar nerve. Prior treatment modalities included cortisone injections, topical capsaicin, lidocaine but no significant change was seen in pain level. tMS treatment was attempted with initial pain score of 5 and post-treatment score of 0. She required repeat treatments at time intervals of four to seven weeks and her pre-treatment pain scores remained 1 to 2 at return visits. The treatment parameters used were frequency of 0.5 Hz, 65% amplitude with 20 pulses per train and average of 20 trains. She is now able to function as a full time veterinarian with barely noticeable pain in her foot.

Example 3

A 51 year old female with history of Crohn's disease and multiple abdominal surgeries presented with right lower quadrant abdominal pain. She was diagnosed with abdominal nerve entrapment with initial pain score of 5. Two neuromas (1.5 cm×1.25 cm) and 1.5 cm×1.0 cm) were identified with palpation. Paresthesia could be elicited with palpation over the neuroma. She received tMS treatments with frequency of 0.5 Hz and amplitude of 60% at incisional scar and right lower quadrant abdominal region. Initially she was treated every 2 weeks and later her treatments were scheduled every 4-6 weeks. Overall her average post-treatment pain score ranged from 0 to 2.

Example 4

A 56 year old male presented with chronic elbow pain with history of left ulnar nerve submuscular transposition. A palpable neuroma (1.0 cm×0.75 cm) was identified with physical examination. Paresthesia along the ulnar aspect of the left forearm could be elicited with movement of the elbow or palpation over the neuroma. He was diagnosed with left elbow neuroma at initial consult visit and physical exam findings were significant for tenderness to palpation over triceps insertion site. His prior treatment modalities utilized were VICODIN®, gabapentin, meloxicam, steroid injections and chiropractic adjustments without significant benefit. tMS treatment was initiated with pre-treatment pain score of 3 and parameters used were frequency of 0.5 Hz and amplitude of 60 to 80% with 20 pulses per train and average of 20 trains. Patient's post-treatment scores were zero and he received treatment every six to eight weeks.

Example 5

A 25 year old male presenting with chronic left groin pain, radiating to anterior and medial thigh, with a history of left inguinal hernia surgery 3 years prior to presentation. The physical exam was significant for tenderness with deep palpation to L groin and flexion elicited pain to left inguinal region as well as up to knee level. He was diagnosed with left inguinal nerve entrapment and his initial pre-treatment pain score was 5. Prior attempts at treating his condition included ibuprofen, LYRICA®, amitryptyline, gabapentin, lidocaine patch and steroid injections. tMS treatment was initiated with frequency of 0.5 Hz and amplitude of 60-70% with 20 pulses per train and average number of 20 trains. Patient reported pain relief with pain scores of 0 to 2 when treatments were scheduled three to four week intervals. His pre-treatment scores ranged from 2 to 4 and post-treatment scores were zero.

A proposal for conducting a sham controlled randomized study is currently being prepared for IRB approval.

VII. Computer-Implemented Embodiment

Figure 12:
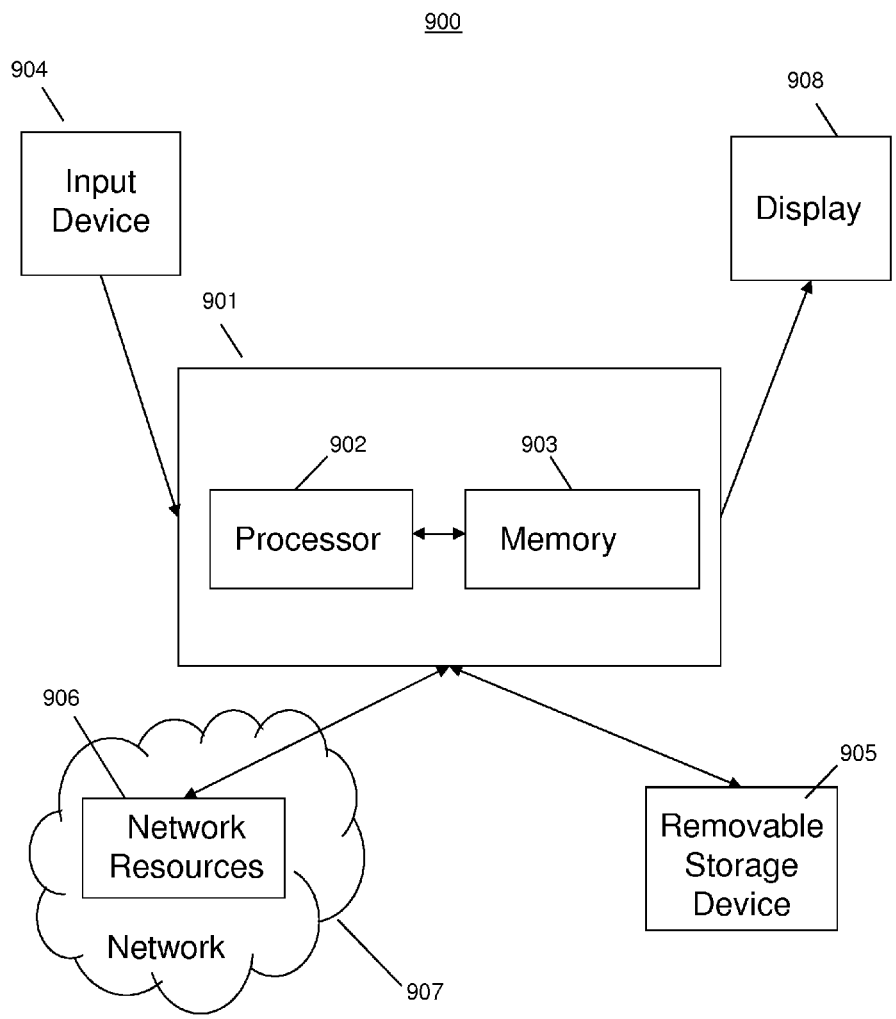
FIG. 12 is a block diagram illustrating an embodiment of a computer/server system upon which an embodiment of the inventive methodology may be implemented.

FIG. 12 is a block diagram that illustrates an embodiment of a computer/server system 900 upon which an embodiment of the inventive methodology may be implemented. The system 900 includes a computer/server platform 901 including a processor 902 and memory 903 which operate to execute instructions, as known to one of skill in the art. The term "computer-readable storage medium" as used herein refers to any tangible medium, such as a disk or semiconductor memory, that participates in providing instructions to processor 902 for execution. Additionally, the computer platform 901 receives input from a plurality of input devices 904, such as a keyboard, mouse, touch device or verbal command. The computer platform 901 may additionally be connected to a removable storage device 905, such as a portable hard drive, optical media (CD or DVD), disk media or any other tangible medium from which a computer can read executable code. The computer platform may further be connected to network resources 906 which connect to the Internet or other components of a local public or private network. The network resources 906 may provide instructions and data to the computer platform from a remote location on a network 907. The connections to the network resources 906 may be via wireless protocols, such as the 802.11 & 802.16 standards, Bluetooth® or cellular protocols, or via physical transmission media, such as cables or fiber optics. The network resources may include storage devices for storing data and executable instructions at a location separate from the computer platform 901. The computer interacts with a display 908 to output data and other information to a user, as well as to request additional instructions and input from the user. The display 908 may therefore further act as an input device 904 for interacting with a user.

What is claimed is:

1. A portable transcutaneous magnetic stimulation (tMS) device for treatment of peripheral nerve pain, comprising:
   a tMS stimulator configured to deliver a focused pulse of magnetic flux to a target body area, the tMS stimulator comprising an insulated magnetic coil in a figure-of-eight shape disposed within a housing, wherein the tMS stimulator produces an output of up to approximately 3 Tesla with 20 kTesla/sec. of instantaneous flux at a frequency of approximately 0.2 Hertz (Hz) to approximately 5 Hz; and
   a control module in powered communication with the tMS stimulator configured to control a pulse rate and a magnetic field of magnetic flux delivered to the target body area.

2. The tMS device of claim 1, wherein the coil in the figure-of-eight shape includes a left coil and a right coil, and wherein the left coil and right coil rotate to adjust a focal point of the treatment being delivered to the target body area.

3. The tMS device of claim 2, wherein the left coil and right coil rotate in a range from a first approximately planar configuration to a second rotated configuration such that an angle between each coil is an approximately obtuse angle.

4. The tMS device of claim 3, wherein the left coil and right coil rotate up to approximately 30 degrees from the first approximately planar configuration to the second rotated configuration.

5. The tMS device of claim 1, wherein the tMS stimulator further includes a magnetometer configured to measure a strength and direction of the magnetic field generated by the insulated magnetic coil.

6. The tMS device of claim 1, wherein the tMS stimulator further comprises an accelerometer configured to detect a magnitude and direction of movement of the tMS stimulator.

7. The tMS device of claim 1, wherein the tMS stimulator further includes a proximity sensor configured to determine whether the tMS stimulator is at the target body area.

8. The tMS device of claim 1, wherein the coil in the figure-of-eight shape includes a left coil and a right coil, and the left coil and right coil rotate simultaneously via a central gear mechanism.

9. The tMS device of claim 1, further comprising a stimulation coil handle which includes a touch-sensitive surface and a built-in display to communicate user interactions to a host system and to display an image to a user.

10. The tMS device of claim 1, further comprising:
   a portable electronic device in wireless communication with the control module and configured to receive data from the control module relating to the delivered magnetic pulse and feedback from a user relating to the delivered magnetic pulse; and
   a remote server in communication with the portable electronic device configured to receive the data from the control module relating to the delivered magnetic pulse and the feedback from the user relating to the delivered magnetic pulse.

11. The tMS device of claim 1, wherein the control module comprises a capacitor bank configured to operate within a range of −2000 to +4500 volts DC.

12. The tMS device of claim 11, wherein the capacitor bank comprises graphene supercapacitors.

13. A method of treating peripheral nerve pain in a patient in need thereof using transcutaneous magnetic stimulation (tMS), comprising the steps of:
   configuring a control module to deliver a specified magnetic field pulse rate and magnetic field strength using a tMS stimulator disposed within a positionable housing;
   positioning the tMS stimulator at a therapeutic position adjacent a target area of a human body experiencing peripheral nerve pain, wherein the tMS stimulator comprises a rotatable magnetic coil in a figure-of-eight shape disposed within the positionable housing, wherein the coil in the figure-of-eight shape includes a left coil and a right coil, and wherein the left coil and right coil rotate with respect to one another to adjust a focal point of a treatment being delivered to the target area of the human body; and
   delivering a low frequency magnetic field pulse at the specified magnetic field pulse rate and magnetic field strength using the tMS stimulator to treat peripheral nerve pain.

* * * * *